United States Patent [19]
Kane

[11] 3,973,561

[45] Aug. 10, 1976

[54] EYE PATCH FOR LARGE DOMESTIC ANIMALS

[76] Inventor: George K. Kane, P.O. Box 360, Sioux Falls, S. Dak. 57101

[22] Filed: June 30, 1975

[21] Appl. No.: 591,348

[52] U.S. Cl. ............................ 128/132 R; 128/163
[51] Int. Cl.² ............................................ A61F 13/00
[58] Field of Search ............ 128/132, 163, 155, 249, 128/154; 2/9, 14, 15

[56] References Cited
UNITED STATES PATENTS

| | | | |
|---|---|---|---|
| 1,642,661 | 9/1927 | Robinson | 128/163 |
| 2,572,638 | 10/1951 | Loos | 128/163 |
| 2,896,615 | 7/1959 | Szigeti | 128/132 R |
| 3,092,103 | 6/1963 | Mower | 128/132 R |
| 3,392,725 | 7/1968 | Behney | 128/249 |
| 3,619,815 | 11/1971 | Towner, Jr. | 2/12 |
| 3,664,340 | 5/1972 | Morgan | 128/249 |

Primary Examiner—John D. Yasko

[57] ABSTRACT

An eye covering for a large domestic animal adapted to protect the eye in the event of an infection or disease. The covering is formed of material such that it is opaque and of a form that causes the covering to spring back to its original form after deflection.

5 Claims, 4 Drawing Figures

EYE PATCH FOR LARGE DOMESTIC ANIMALS

BACKGROUND AND SUMMARY OF THE INVENTION

This invention pertains to eye coverings for domestic animals, especially bovine animals, and more particularly to a covering for a single eye to protect that eye from irritation and damage in the event of an infection or disease in the eye.

Cattle, among larger domestic animals, are especially subject to diseases of the eye such as "pink eye". When this disease is contracted, it is important that the affected eye be covered and protected from dust and the like and particularly from bright sunlight. In order to do this, an opaque shield is necessary.

It is also desirable that a protector should be resilient rather than hard or brittle. The resilient shield will withstand much more impact and abrasion than the more rigid shields. Therefore, it will last longer. However, the resilience must not be such that the material holds a permanent deformation. The shield must adapt to a bit of deformation but must spring back into a shape to keep from damaging the eye over which it is used.

My invention accomplishes these desirable features particularly because of its shape and the material of which it is constructed.

FIGURES

DESCRIPTION

Figure 1:
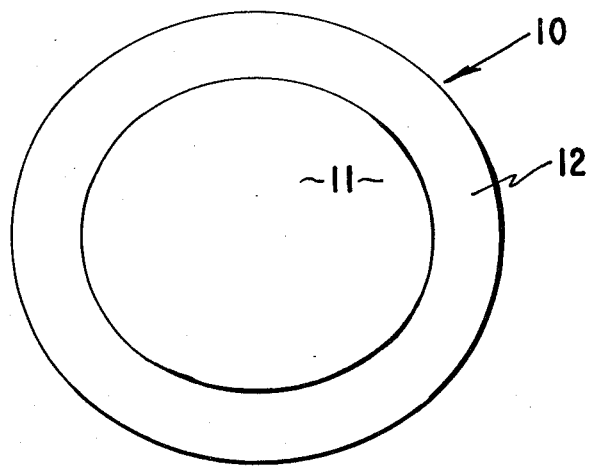
FIG. 1 is a top plan view of my device.
Figure 2:
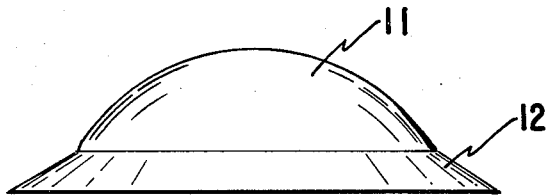
FIG. 2 is a side elevational view of the device of FIG. 1.
Figure 4:
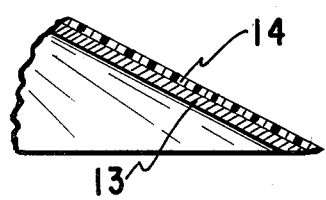
FIG. 4 is an added partial sectional view to a greater enlarged scale showing the lamination of the material.
Figure 3:
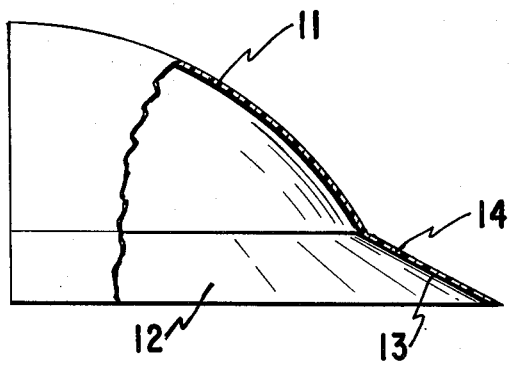
FIG. 3 is a partial sectional view to an enlarged scale of the device.

The device of my invention is an inexpensive eye shield for large domestic animals to be used in the event of illness or infection in the eye. The shield is shaped to provide sufficient resilience so that when deflected it will, upon release of the deflecting force, spring back into its original shape.

More specifically and referring to the drawings I provide a shield 10 in the form of a dome 11. A flange 12 is provided at the edge of the dome.

The dome is in the form of an ellipsoid having a basic plan form of an ellipse with a major axis approximately 1⅛ times its minor axis. This forms a shape which readily conforms to the eye to be covered, and also provides a dome which springs back to shape after it has been deformed.

The flange is in the form of a truncated cone having a base angle of approximately 30°. This angle allows the flange to lie against the head of the animal so that it can be held in place by means of a cement. The dome then bulges above the eye and is clear of the eye to avoid irritation.

The entire device is molded from a laminated plastic material. The principal structural material 13 is a semi-rigid, cross linked, closed cell, foamed polyethylene sheet material approximately 0.06 to 0.131 inches thick. This material normally is opaque when formed. Because any light allowed to infiltrate would be irritating to an infected eye, I feel it is necessary that the dome be opaque.

The foamed material, while opaque and able to hold its shape, is also relatively soft and very subject to abrasion. It then becomes necessary to build in some abrasion resistance. Therefore, I use a thin film 14 of low density, polyethylene film laminated onto the basic material. The film may range from 6 to 10 mils in thickness. The low density film, because of its thinness, does not substantially contribute to nor detract from the basic structural resilience. In order to keep the temperature beneath the cover to reasonable values, I prefer that the outer film be of light or white color to reflect the sun's heat. The outer material being somewhat abrasion resistant is able to protect the foamed material from damage caused by the animal rubbing the patch against posts or the like. Thus, I provide both a resilient and an opaque structure uniquely adapted for the use to which it is to be put.

I claim:

1. An eye shield adapted to cover the eye of a large domestic animal comprising a cover of dome shape with a flange attached to said dome shape, said cover being formed of a laminated material having a resilient opaque base material and an abrasion-resistant film laminated with said base material, and adhesive securing means on said flange whereby said cover is attachable to said animal.

2. The device of claim 1 in which the dome shape is in the form of an ellipsoid having a major axis approximately 1⅛ times the minor axis.

3. The device of claim 1 in which said cone shape is formed with a base angle of approximately 30°.

4. The device of claim 1 in which the base material is a semi-rigid, cross linked, closed cell, foamed polyethylene material having a thickness between 0.06 and 0.131 inches and the film is a dense, abrasive resistant polyethylene film having a thickness of between 6.0 and 10.0 mils.

5. The device of claim 4 in which the film has a white colored outer surface.

* * * * *

UNITED STATES PATENT OFFICE
CERTIFICATE OF CORRECTION

Patent No. 3,973,561  Dated August 10, 1976

Inventor(s) George K. Kane

It is certified that error appears in the above-identified patent and that said Letters Patent are hereby corrected as shown below:

Claim 3 should read:

3. The device of claim 1 in which said flange is a cone shape formed with a base angle of approximately 30 degrees.

Signed and Sealed this

Eighteenth Day of March 1980

[SEAL]

Attest:

SIDNEY A. DIAMOND

Attesting Officer  Commissioner of Patents and Trademarks